(12) United States Patent
Marcinek et al.

(10) Patent No.: US 8,377,972 B2
(45) Date of Patent: Feb. 19, 2013

(54) USE OF QUATERNARY PYRIDINIUM COMPOUNDS FOR VASOPROTECTION AND/OR HEPATOPROTECTION

(75) Inventors: Andrzej Marcinek, Łódź (PL); Stefan Chłopicki, Kraków (PL); Jerzy G Ębicki, Łódź (PL); Jan Adamus, Łódź (PL)

(73) Assignee: Trigendo Sp. zo.o., Cracow (PL)

( * ) Notice: Subject to any disclaimer, the term of this patent is extended or adjusted under 35 U.S.C. 154(b) by 103 days.

(21) Appl. No.: 13/011,364

(22) Filed: Jan. 21, 2011

(65) Prior Publication Data

US 2011/0118316 A1    May 19, 2011

Related U.S. Application Data

(63) Continuation of application No. 12/038,381, filed on Feb. 27, 2008, now Pat. No. 7,893,095.

(30) Foreign Application Priority Data

Feb. 28, 2007    (PL) .......................... 381862

(51) Int. Cl.
*A61K 31/44*    (2006.01)
(52) U.S. Cl. ....................................... 514/358
(58) Field of Classification Search .................. 514/358
See application file for complete search history.

(56) References Cited

U.S. PATENT DOCUMENTS

2005/0267015 A1    12/2005    Batarseh
2006/0292252 A1    12/2006    Bhaskaran et al.

FOREIGN PATENT DOCUMENTS

| WO | WO 2004/009034 A2 | 1/2004 |
| WO | WO 2005/067927 A2 | 6/2005 |
| WO | WO 2006/024545 A1 | 3/2006 |
| WO | WO 2006/136454 A2 | 12/2006 |
| WO | WO 2007/103540 A2 | 3/2007 |

OTHER PUBLICATIONS

Stadler, R.H., et al., "Alkylpyridiniurns. 1. Formation in Model Systems via.Thermal Degradation of Trigonelline," *J. Agric. Food Chem.* 50:1192-1199, American Chemical Society (2002).
Stadler, R.H., et al., "Alkylpyridiniums. 2. Isolation and Quantification in Roasted and Ground Coffees," *J. Agric. Food Chem.* 50:1200-1206, American Chemical Society (2002).
Brooks, A.I., et al., "Paraquat elicited neurobehavioral syndrome caused by dopaminergic neuron loss," *Brain Res.* 823:1-10, Elsevier/North-Holland Biomedical Press (1999).
Chacón, J.N., and Truscott, T.G., "Chemically induced Parkinson's disease. III: a study of a possible role of singlet molecular oxygen in Parkinson's disease," *J. Photochem. Photobiol. B.* 11:261-267, Elsevier Sequoia (1991).
Cicchetti, F., et al., "Systemic exposure to paraquat and maneb models early Parkinson's disease in young adult rats," *Neurobiol. Dis.* 20:360-371, Academic Press (2005).

Lee, E.-S., and Charlton, C.G., "1-Methyl-4-phenyl-pyridinium increases S-adenosyl-L-methionine dependent phospholipid methylation," *Pharmacol. Biochem. Behav.* 70:105-114, Elsevier (2001).
Nagatsu, T., and Hirata, Y., "Inhibition of the Tyrosine Hydroxylase System by MPTP, 1-Methyl-4-phenylpyridinium Ion ($MPP^+$) and the Structurally Related Compounds in vitro and in vivo," *Eur. Neurol.* 26 (*supp 1*):11-15, Karger (1987).
Rollema, H., et al., "In vivo Intracerebral Microdialysis Studies in Rats of $MPP^+$ *Analogues and Related Charged Species*," *J. Med. Chem.* 33:2221-2230, American Chemical Society (1990).
Watanabe, K., et al., "Paraquat Depresses the Activity of Angiotensin Converting Enzyme Expressed by Human Umbilical Vein Endothelial Cells in Culture," *Cell. Biol. Int. Rep.* 15:205-210, International Federation for Cell Biology (1991).
Williams, A.C., et al., "Idiopathic Parkinson's Disease: A Genetic and Environmental Model," *Adv. Neurol.* 80:215-218, Lippincott Williams & Wilkins (1999).
STN Database, Accession No. 1310 (1989:188332), "Anticholineesterase activity of alkaloid idomethylates" (accessed Jul. 2008).

(Continued)

*Primary Examiner* — Raymond Henly, III
(74) *Attorney, Agent, or Firm* — Sterne, Kessler, Goldstein & Fox P.L.L.C.

(57) ABSTRACT

The invention relates to a method for the treatment or prevention of diseases or conditions associated with vascular endothelium dysfunction or liver injury comprising the administration to a patient in a need of such treatment or prevention of a therapeutically or prophylactically effective amount of a compound selected from the group consisting of:

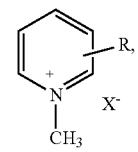

(I)

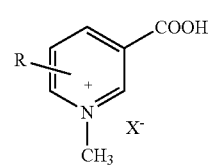

(II)

and

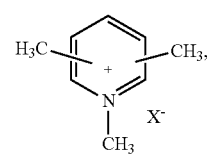

(III)

wherein R represents hydrogen atom, $CH_3$, OH, pyridyl ($C_5H_4N$), 1-methylpyridyl ($C_5H_4N-CH_3$) or pyridyl substituted with hydroxy group (($OH)C_5H_3N$), and X represents a physiologically acceptable counterion.

11 Claims, 4 Drawing Sheets

OTHER PUBLICATIONS

STN Database, Accession No. 1313 (1969:448218), "Antiatherosclerotic drugs and fibrinolysis" (accessed Jul. 2008).

International Search Report for International Application No. PCT/IB2008/050666, mailed on Aug. 4, 2008, European Patent Office, Rijswijk, Netherlands.

Written Opinion for International Application No. PCT/IB2008/050666, mailed on Aug. 4, 2008, European Patent Office, Munich, Germany.

Chlopicki, S., et al.,"1-Methylnicotinamide (MNA), a primary metabolite of nicotinamide, exerts anti-thrombotic activity mediated by a cyclooxygenase-2/prostacyclin pathway," *Br J Pharmacol*: 152(2): 230-9 (Sep. 2007).

Grigor'eva, G.M. et al., "[Anticholinesterase activity of alkaloid iodomethylates,]" *Dokl Akad Nauk SSSR*:304(3):746-8 (Jan 1989).

De Nicola, P. et al., "Antiatherosclerotic drugs and fibroinolysis" Int. Congr. Gerontol., Proc., 7th, vol. 2, pp. 441-443 publisher: Verlag Wien. Med. Akad., Vienna, Austria, 1966, pp. 441-443.

Fig. 1 Scheme of the method for detection of thrombolytic action of drugs *in vivo* in rats (according to Gryglewski et al..)

Fig. 2. The effect of *in vivo* intravenous administration of nicotinamide or nicotinic acid (30 mg/kg).

Fig. 3. The effect of *in vivo* intravenous administration of trigonelline (30 mg/kg).

Fig. 4. The thrombolytic response induced by *in vivo* intravenous administration of trigonelline thermolysate (30 mg/kg).

Fig. 5. The thrombolytic response *in vivo* induced by intravenous administration of 1-methylpyridinium chloride (30 mg/kg) (upper record) and 1,4-dimethyl-pyridinium chloride (30 mg/kg) (lower record).

Fig. 6. The effect of trigonelline thermolysate on postprandial hyperglycemia in comparison with metformin and non-treated control.

Fig. 7. The hepatoprotective effect of 1,4-dimethylpyridinium chloride *in vivo*.

USE OF QUATERNARY PYRIDINIUM COMPOUNDS FOR VASOPROTECTION AND/OR HEPATOPROTECTION

This application is a continuation of U.S. patent application Ser. No. 12/038,381, now U.S. Pat. No. 7,893,095.

FIELD OF THE INVENTION

The present invention relates to a method of treatment or prevention of diseases or conditions associated with endothelium dysfunction or liver injury. In particular, the method comprises the administration of certain quaternary pyridinium compounds to a subject in a need of such treatment.

The invention is based on the unique ability of certain quaternary pyridinium compounds to stimulate endogenous production and release of prostacycline $PGI_2$ in vascular endothelium which can bring therapeutic effects in diseases associated with endothelial dysfunction, oxidative stress and insufficient endothelial $PGI_2$ production, as well as in the conditions of enhanced risk of incidence of said diseases (vasoprotective effect). The use of such compounds can provide healing and preventive therapeutic effects among others in diabetes, metabolic syndrome, atherosclerosis and also in liver injuries (hepatoprotective effect).

BACKGROUND ART

There is increasing evidence that endothelial dysfunction plays a key role in the formation and progression of atherosclerotic plaque as well as in the development of diabetes and diabetic complications. Endothelial dysfunction has recently gained diagnostic, prognostic and therapeutic significance in atherothrombosis and diabetes (Heitzer T, Schlinzig T, Krohn K, Meinertz T, Munzel T. Endothelial dysfunction, oxidative stress, and risk of cardiovascular events in patients with coronary artery disease. *Circulation* 2001; 104:2673-2678; Schachinger V, Britten M B, Zeiher A M. Prognostic impact of coronary vasodilator dysfunction on adverse long-term outcome of coronary heart disease. *Circulation* 2000; 101: 1899-1906; Perticone F, Ceravolo R, Pujia A, Ventura G, Iacopino S, Scozzafava A, Ferraro A, Chello M, Mastroroberto P, Verdecchia P, Schillaci G. Prognostic significance of endothelial dysfunction in hypertensive patients. *Circulation* 2001; 104:191-196; Suwaidi J A, Hamasaki S, Higano S T, Nishimura R A, Holmes D R, Jr., Lerman A. Long-term follow-up of patients with mild coronary artery disease and endothelial dysfunction. *Circulation* 2000; 101:948-954), de Jager J, Dekker J M, Kooy A, Kostense P J, Nijpels G, Heine R J, Bouter L M et al.: Endothelial dysfunction and low-grade inflammation explain much of the excess cardiovascular mortality in individuals with type 2 diabetes: the Hoorn Study. *Arterioscler Thromb Vasc Biol,* 2006, 26, 1086-1093).

Endothelial dysfunction is defined as a functional endothelium condition which is characterized by deficiency of vasoprotective factors and enhanced production of pro-coagulative and pro-inflammatory factors (Chlopicki S, *Kardiologia po Dyplomie,* 2005, Vol. 4 No. 5, 77-88). Clinically, endothelial dysfunction is identified as the impairment of biological activity of NO, which is diagnosed as the impairment of vasodilating NO activity. Monitoring of bioavailability of NO is possible by measurement of NO-dependent vasoconstrictive endothelium function in vivo (Chlopicki S, *Kardiologia po Dyplomie,* 2005, Vol. 4 No. 5, 75-81). The impairment of NO activity coincides with oxidant stress (Heitzer T, Schlinzig T, Krohn K, Meinertz T, Munzel T. Endothelial dysfunction, oxidative stress, and risk of cardiovascular events in patients with coronary artery disease. *Circulation* 2001; 104:2673-2678) and impairment of $PGI_2$ synthesis (Kyrle P A, Minar E, Brenner B, Eichler H G, Heistinger M, Marosi L, Lechner K. Thromboxane $A_2$ and prostacyclin generation in the microvasculature of patients with atherosclerosis—effect of low-dose aspirin. *Thromb Haemost* 1989; 61:374-377), although systemic level of $PGI_2$ may be elevated. Indeed, it has been proposed that increased lipid peroxidation might promote development of atherosclerosis owing to selective impairment of prostacyclin synthesis in endothelial cells and subsequent activation of platelets (Gryglewski R J. Prostacyclin and atherosclerosis. *TIPS* 1980; 1: 164-168; Gryglewski R J. Prostaglandins, platelets, and atherosclerosis. *CRC Crit. Rev Biochem* 1980; 7:291-338; Gryglewski R J, Szczeklik A. Prostacyclin and atherosclerosis—experimental and clinical approach. 1983; 213-226). This concept was then supported experimentally. It is apparent now that impairment of $PGI_2$ synthesis in endothelium may lead to the excessive stimulation of TP receptors in endothelium and vascular smooth muscle cells by $TXA_2$, $PGH_2$ or other eicosanoids. Such mechanisms lead to subsequent vasoconstriction, platelet activation, inflammatory response of endothelium as well as endothelial apoptosis (Chlopicki S, Gryglewski R J. Endothelial secretory function and atherothrombosis in "The Eicosanoids", chapter 23, 267-276. ed. P. Curtis-Prior, John Wiley and Sons, Ltd, 2004). This means that the impairment of $PGI_2$ synthesis in endothelium may trigger or enhance inflammatory and thrombotic processes in vascular wall, which are now considered to be the key elements of atherosclerosis. Endothelial dysfunction plays also the key role in the development of diabetes (de Jager J, Dekker J M, Kooy A, Kostense P J, Nijpels G, Heine R J, Bouter L M et al.: Endothelial dysfunction and low-grade inflammation explain much of the excess cardiovascular mortality in individuals with type 2 diabetes: the Hoorn Study. *Arterioscler Thromb Vasc Biol,* 2006, 26, 1086-1093.) Therefore, the result of the ability of certain quaternary pyridinium salts to stimulate endothelial $PGI_2$ synthesis can be their potential anti-atherosclerotic and anti-diabetic effects. Similarly, in many other diseases wherein endothelial dysfunction plays a role in pathogenesis, pharmacological enhancement of $PGI_2$ synthesis in endothelium caused by said compounds may bring therapeutic effects. Some of quaternary pyridinium salts can also have therapeutic effects in diseases responding to prostacycline analogs, such as for example liver injuries, pulmonary hypertension, and wound healing.

The use of quaternary pyridinium salts of the formula:

wherein R is $NH_2$, $CH_3$, or $N(H)CH_2OH$ group, and X is pharmaceutically acceptable counterion, for the preparation of vasoprotective agent for the treatment or prevention of conditions or diseases associated with dysfunction of vascular endothelium, oxidative stress, and/or insufficient production of endothelial prostacyclin $PGI_2$ is described in WO2005/067927. In particular, anti-atherosclerotic and thrombolytic activity of the compounds of the above formula was shown.

In publications of R. Stadler et al. in. w J. Agric. Food Chem. 2002, 50, 1192-1199 and 1200-1206 products of trigonelline decomposition formed during coffee roasting were reported. Reportedly, the main non-volatile products of trigonelline pyrolysis were 1-methylpyridine and dialkylpyridinium compounds. Potential anticancer activity of alkylpyridinium compounds, especially 1-methylpyridine, was suggested.

SUMMARY OF THE INVENTION

In brief, the invention relates to a method for the treatment or prevention of diseases or conditions associated with vascular endothelium dysfunction or liver injury comprising the administration to a patient in a need of such treatment or prevention of a therapeutically or prophylactically effective amount of a compound selected from the group consisting of:

wherein R represents hydrogen atom, $CH_3$, OH, pyridyl ($C_5H_4N$), 1-methylpyridyl ($C_5H_4N$—$CH_3$) or pyridyl substituted with hydroxy group (($OH)C_5H_3N$), and X represents a physiologically acceptable counterion.

DETAILED DISCLOSURE OF THE INVENTION

The aim of the present invention was to provide new therapeutic agent, having vasoprotective and/or hepatoprotective activity and therefore the potential utility for the treatment and prevention of among others atherosclerosis, thrombosis, diabetes, metabolic syndrome, and liver injuries of different origin.

It has been unexpectedly and surprisingly found that some compounds that are formed during the process of thermal decomposition of trigonelline show vasoprotective activity as well as hepatoprotective activity due to their ability to improve endothelial function by stimulation of the release of endogenous prostacycline.

Accordingly, a subject of the invention is a method for the treatment or prevention of diseases or conditions associated with vascular endothelium dysfunction or liver injury comprising the administration to a patient in a need of such treatment or prevention of a therapeutically or prophylactically effective amount of a compound selected from the group consisting of:

wherein R represents hydrogen atom, $CH_3$, OH, pyridyl ($C_5H_4N$), 1-methylpyridyl ($C_5H_4N$—$CH_3$) or pyridyl substituted with hydroxy group (($OH)C_5H_3N$), and $X^-$ represents a physiologically acceptable counterion.

As defined above, $X^-$ may be any organic or inorganic physiologically acceptable anion, i.e. such an anion which is devoid of any toxic or otherwise harmful effect to a body, in particular acceptable for oral administration in therapeutic doses.

Non-limiting examples of suitable physiologically acceptable inorganic anions are chloride, bromide, iodide and carbonate. Non-limiting examples of suitable physiologically acceptable organic anions are anions of mono-, di- and tricarboxylic acids, for example acetate, benzoate, salicylate, hydroxyacetate, lactate, malonate and citrate, etc.

Preferred physiologically acceptable anion is chloride.

In one of the embodiments the compound has the formula (I)

wherein R represents hydrogen atom or CH$_3$ in the position 2 or 4 of the pyridine ring.

One of the preferred embodiments is the compound of the formula

(I)

wherein R represents CH$_3$ in the position 4 of the pyridine ring.

Particular compounds useful in the method of the invention are 1,4-dimethylpyridine salts, especially chloride, lactate or citrate, especially advantageously 1,4-dimethylpyridine chloride of the formula:

Another particular compounds useful in the method of the invention are 1,2-dimethylpyridine salts, especially chloride, lactate or citrate, especially advantageously 1,2-dimethylpyridine chloride of the formula:

Yet another particular compounds useful in the method of the invention are 1-methylpyridine salts, especially chloride, lactate or citrate, especially advantageously 1-methylpyridine chloride of the formula:

Pyridinium compounds of formulae (I), (II) and (III) can be obtained by chemical synthesis, using conventional techniques known for a person skilled in the art of organic synthesis.

Said compounds can be for example obtained starting from corresponding known compounds non-substituted with methyl group at the nitrogen atom of the pyridine ring, i.e. at position 1 of the pyridine ring. When X$^-$ represents halogenide anion, compounds of formulae (I), (II) and (III) can be obtained by direct methylation with methyl halogenide from starting materials non-substituted with methyl group at the nitrogen atom, in a manner known per se. Compounds wherein X$^-$ represents chloride anion can be for example obtained by treating with methyl chloride a starting compound non-substituted with methyl group in position 1, as described for example in AT 131,118, GB3 48345, U.S. Pat. No. 3,614,408, and U.S. Pat. No. 4,115,390.

Compounds wherein X$^-$ is an anion other than halogenide can be obtained by the exchange of halogenide anion with another anion, for example by the treatment with a salt of such another anion, for example silver salt. For example, lactates or acetates of the above compounds can be obtained by treating a halogenide, preferably chloride, with a salt of another anion, for example silver salt. For example, lactates or acetates of the above compounds can be obtained by treating a halogenide, preferably chloride, with solver lactate or acetate, respectively.

The above compounds of formulae (I), (II) and (III) are produced in a process of thermal decomposition (thermolysis) of trigonelline (N-methylnicotinic acid, 3-carboxy-1-methylpyridinium salt). Individual compounds of formulae (I), (II) and (III) can be therefore obtained also by separation of the products of pyrolysis of trigonelline (thermolysate), obtained for example by pyrolysis in the oxygen-free atmosphere at about 220° C.

Thus, in one of embodiments of the method of the invention a mixture of the compounds selected from the above defined compounds of formulae (I), (II) and (III) can be used, as comprised in the product of thermal decomposition of trygonelline, i.e. trigonelline thermolysate.

It has been found that pyridinium compounds defined above posess unique pharmacological properties due to their ability to release endogenous prostacycline (PGI$_2$) from endothelium. In consequence, the compounds can improve tissue perfusion, exert anti-thrombotic, thrombolytic, anti-apoptotic or antisclerotic activity, protect gastrointestinal mucosa, as well as exert hepatoprotective activity in the treatment or prevention of liver injuries.

The advantage of the above pyridinium compounds is the fact that their vasoprotective activity is most probably not accompanied by any hypotensive action. Furthermore, thrombolytic activity is not connected with direct action on blood platelets. The above pyridinium compounds do not have any direct action on leucocytes activity.

Without any wish to be bound by theoretical considerations, the present inventors believe that the compounds defined in the present invention, being endowed with a positive charge, bound through electrostatic interactions with anionic compounds present on the surface of vascular endothelium, such as glycosaminoglycans. The consequences of such bonding can be several endothelial effects, which effects can have positive influence from the pharmacological point of view. Among such effects can be the release of NO and/or prostacycline, due to which endothelial dysfunction can be improved and conditions or diseases associated with such dysfunction can be treated or prevented.

In one of the aspects of the method of the invention such conditions or diseases associated with endothelial dysfunction are those associated with endothelial dysfunction accompanied by hypercholesteremia, hypertriglycerydemia or low HDL cholesterol level.

In one of particularly preferred embodiments of the above aspect disease or condition is thrombosis or atherosclerosis.

In another aspect of the method of the invention said disease or condition can be an acute cardiovascular event associated with atherosclerosis, in particular sudden cardiac death, acute coronary syndrome (including unstable coronary artery disease, myocardial infarct), a condition which necessitates the coronary angioplasty (PCI) or coronary-aortal by-pass surgery (CABG), ischemic stroke, surgical treatment with extracorporeal circulation or a condition which necessitates a peripheral circulation revascularization.

In another aspect of the method of the invention said condition or disease is atherosclerosis in a patient with stable coronary disease, brain ischemic episodes or atherosclerosis of extremities, including Burger disease.

In yet another aspect of the method of the invention said condition or disease is selected from the risk factors of atherosclerosis selected from the group consisting of: hypercholesterolemia, arterial hypertension, smoking, hyperhomocysteinaemia, insulin resistance, metabolic syndrome, type-2 diabetes, menopause, aging, obesity, mental stress, infections, inflammatory states, including periodontal disease, rheumatoid arthritis, allograft vasculopathy and nitrate tolerance.

In yet another aspect of the method of the invention said condition or disease is dyslipidemia, in particular hypercholesterolemia or hypertriglyceridemia, including dyslipidemia associated with low plasma level of HDL.

In yet another aspect of the method of the invention said condition or disease to be treated or prevented is selected from the group consisting of: chronic cardiac failure, pulmonary hypertension, microvascular diabetic complications, diabetic neuropathy, nephrotic syndrome, chronic renal failure, adults respiratory distress syndrome (ARDS), cystic fibrosis, chronic obstructive pulmonary disease (COPD), preeclampsia/eclampsia, erectile dysfunction, Stein-Leventhal syndrome, sleep apnea, systemic lupus erythematosus, sickle cell anemia, non-specific inflammatory bowel diseases, gastric or duodenal ulcers, glaucoma, chronic liver disease, primary amyloidosis, and neurodegenerative diseases.

Said neurodegenerative disease can be in particular selected from vascular dementia, Alzheimer's disease and Parkinson's disease.

In another variant said condition or disease can be in particular selected from gastric or duodenal ulcer wherein said compounds exert gastroprotective action.

In yet another aspect of the method of the invention said condition or disease is liver injury wherein said compounds exert hepatoprotective action.

is Said liver injury can be in particular acute liver failure, chronic liver failure or liver cirrhosis.

Said liver injury can be also drug-induced liver injury caused by using medicaments, such as steroids, antifungal agents, antibiotics, immunosupressants, etc. The composition comprising said pyridinium compounds can be used prophylactically to protect liver in the case of taking medicaments having hepatotoxic side effects. Said liver injury can be also alcohol-induced liver injury caused by alcohol abuse, toxic liver injury caused by toxic chemicals, such as for example solvents, including carbon tetrachloride, chloroform, or by pesticides, or liver injury caused by viral hepatitis.

The dosage will depend on the condition or disease being treated, the type of treatment (therapeutic or preventive), the state and the age of a patient being treated, and shall be finally determined individually by a medical practitioner. Generally, the amount of the pyridinium compound or mixture of pyridinium compounds administered shall be in the range of about 0.1 to 10000 mg for administration in one single dose or in divided doses, for example 0.5 mg to 1,125 mg, 1 mg to 1100 mg, 1.25 mg to 1075 mg, 1.5 mg to 1050 mg, 2.0 mg to 1025 mg, 2.5 mg to 1000 mg, 3.0 mg to 975 mg, 3.5 mg to 950 mg, 4.0 mg to 925 mg, 4.5 mg to 900 mg, 5 mg to 875 mg, 10 mg to 850 mg, 20 mg to 825 mg, 30 mg to 800 mg, 40 mg to 775 mg, 50 mg to 750 mg, 100 mg to 725 mg, 200 mg to 700 mg, 300 mg to 675 mg, 400 mg to 650 mg, 500 mg, or 525 mg to 625 mg. In another embodiment the amount of the pyridinium compound(s) included in the administered composition shall be from 0.1 mg to 25 mg. In some embodiments the amount of the pyridinium compound(s) included in the administered composition shall be lower than 100 mg, or lower than 80 mg, or lower than 60 mg, or lower than 50 mg, or lower than 30 mg, or lower than 20 mg, or lower than 10 mg, or lower than 5 mg, or lower than 2 mg, or lower than 0.5 mg.

In the method of the invention pyridinium salts as defined above can be administered as pharmaceutical compositions or diet supplements in a form for oral administration or ingestion. Such forms can include conventional pharmaceutical. Forms for oral administration, such as tablets, hard and soft capsules, powders, granules, solutions, suspensions, etc. They will include excipients (non-active ingredients) typically used in the art of formulation of pharmaceutical dosage forms, such as carriers, fillers, tabletting aids, flavour agents, etc. Each of such excipients must be "acceptable", i.e. must be compatible with other ingredients of the formulation, in particular with the active ingredient and must not be noxious for a patient. Non-limiting examples of such materials which can be used as pharmaceutically acceptable carriers and fillers are: sugars, such as lactose, glucose and saccharose; starches, such as corn starch and potato starch; cellulose and cellulose derivatives, such as carboxymethylcellulose, ethylcellulose, hydroxypropylcellulose, cellulose acetate, microcrystalline cellulose; tragacanth; polyvinylpyrrolidone; calcium phosphate. Formulation for oral administration can also include lubricants and flow improving agents, such as stearates, for example magnesium stearate, talc or silica; disintegrating agents, such as for example sodium starch glycolate. Tablets can be coated with conventional coatings or sustained release coatings.

Liquid formulations for oral administration include solutions, syrups or suspensions. The suitable vehicle is water. They can include also conventional conservants, typically used for inhibition of microorganism growth, such as for example parabens, ascorbic acid, thimerosal, sorbic acid, methyl or propyl p-hydroxybenzoate, etc.

The compounds can be also administered parenterally in a form of intravenous or subcutaneous injections. Suitable vehicles are pyrogen-free water, isotonic saline, phosphate buffers, Ringer's solution, oleaginous carriers, and other non-toxic substances used for the formulation of pharmaceutical dosage forms. They can include isotonicity agents, such as sodium chloride, sugars or polyalcohols, such as mannitol or sorbitol, and stabilizers or conservants.

The compounds can be also administered by inhalation, especially in the case of the treatment of chronic obstructive pulmonary disease. In particular, the compounds can be administered by inhalation in a form of a micronized powder or sprayed aerosol. They can be also administered intranasally in a form of sprayed aerosol. Rectal administration of the compounds in the method of the invention is also contemplated, in a form of creams, ointments or suppositories. In any case, the formulation will incorporate recipients, carriers and vehicles suitable for a given dosage form.

Dosage forms indicated above do not limit in any way the manner of administration of the pyridinium compounds or the compositions containing thereof.

The descriptions of typical and conventional formulations, techniques of their preparation and excipients can be for example found in the Remington: The Science and Practice of Pharmacy, 21 Ed., 2005.

For use in the method of the invention pyridinium compounds can be formulated as diet supplements. Pyridinium compounds can be in accordance with the invention administered being added to nutritional products of any form, typically in the amount of at least 5% by weight of the nutritional product, without being limited to the given contents.

As non-limiting examples, nutritional products can be in a form of a liquid, emulsion or paste, such as beverages, including soft drinks and alcoholic drinks, milk drinks, milk products such as yoghurts. Another example can be solid products such as for example candies, chewing gums, jellies, chocolates, and powdered products, for example powdered drinks for dissolution in water before consumption.

For use in the method of the invention pyridinium compounds can be also added to vitamin supplements in a solid form, such as tablets, capsules, powder for dissolution, or a drink, containing besides the compound of formulae (I), (II) or (III) typical ingredients of vitamin supplements.

The examples below illustrate the use and pharmacological activity of pyridinium compounds according to the invention.

EXAMPLE 1

The Preparation of Trigonelline Thermolysate

Trigonelline thermolysate was prepared by thermal degradation (pyrolysis) of trigonelline at 220° C. for 30 minutes. Trigonelline (in a form of a thin layer of crystals) was pyrolysed in a thin-wall glass ampoule filled with argon.

The resulting mixture of the pyrolysis products was dissolved in water, the solution was filtered and extracted with chloroform. Water was distilled off using rotary evaporator and the residue was dried over phosphorus pentoxide.

Preliminary analysis of the pyrolysis products (thermolysate) by means of the mass spectrometry technique ToF-SIMS (Time of Flight Secondary Ion Mass Spectrometry) is presented below.

TABLE 1

| SIMS analysis-composition of trigonelline thermolysate; identified compounds | | | |
|---|---|---|---|
| Product | Structure | m/e | Peak intensity |
| $C_5H_5N$ |  | 79 | 9265 |
| $C_5H_5NH$ |  | 80 | 3305 |
| $C_5H_5NCH_3$ |  | 94 | 480657 |
| $CH_3(C_5H_4)NCH_3$ |  | 108 | 14580 |
| $CH_3CH_3(C_5H_3)NCH_3$ |  | 122 | 3472 |

TABLE 1-continued

SIMS analysis-composition of trigonelline thermolysate; identified compounds

| Product | Structure | m/e | Peak intensity |
|---|---|---|---|
| COOH(C$_5$H$_4$)NCH$_3$ | | 138 | 87964 |
| CH$_3$COOH(C$_5$H$_3$)NCH$_3$ | | 152 | 25725 |
| CH$_3$Npyr-pyrN | | 171 | 31922 |
| CH$_3$Npyr-pyrNCH$_3$ | | 186 | 2206 |
| OHpyr-COOH(C$_5$H$_3$)NCH$_3$ | | 231 | 30048 |

The major product of the pyrolysis is probably 1-methylpyridinium cation, which is predominant in the spectrum. Other products present in significant amounts are 1,2- and 1,4-dimethylpyridinium cations, and cations of: methyltrigonelline, (2'-hydroxypyridine)trigonelline, N-methyl(pyridine)pyridinium and N-methyl(N'-methylpyridine)pyridinium.

EXAMPLE 2

Binding of Pyridinium Cations to Immobilized Heparin as an Indicator of Thrombolytic Response Research conducted by the inventors indicated a strong correlation of the binding of compounds of interest to heparin which could be related to the presence of the positively charged pyridinium cation in their structure, and the thrombolytic activity of the compounds. Neither binding nor thrombolytic activity were observed for uncharged pyridine derivatives, like for example other nicotinamide metabolites.

The presence of the heparin in the pyridinium salt solution changes the absorption spectrum of the salt through the non-specific electrostatic interactions of pyridinium cations with negatively charged heparin moieties. The use of water-insoluble sepharose-immobilized heparin which binds some fraction of pyridinium cations causes the decrease of the concentration of the salt in the solution. It should be emphasized that sepharose immobilizing agent does not bind with pyridinium cations.

At the high excess of the immobilized heparin in relation to the pyridinium salt concentration the degree of binding depends only on the heparin concentration. It allows, by using the experimental methodology described below, to estimate the degree of binding of different pyridinium compounds to heparin, provided that analogical concentrations of pyridinium salts and constant concentration of sepharose-immobilized heparin are used.

Methodology of the Measurement of the Binding of Pyridinium Cations to Immobilized Heparin To estimate a degree of binding of the pyridinium compounds with heparin spectrophotometric method based on the absorption measurements of aqueous solutions of tested compounds at 20÷100 μM before and after a contact with heparin was used.

Aqueous solutions of tested compounds were added to the suspension of immobilized heparin (Heparin Sepharose CL-6B, Amersham Biosciences AB, Sweden) (25 mg/mL) in ultrapure water from Millipore-Milli-Q system and incubated for 5 minutes. The suspensions of immobilized heparin with the tested compounds were then placed into Eppendorf microtubes and centrifuged at 13 000 rpm for 4 minutes using FORCE 1418 microcentrifuge from Labnet Int. (Edison, N.J., USA). The UV-Vis absorption spectra of the resulting clear supernatants was measured with Perkin Elmer Lambda 40 spectrophotometer. All measurements were performed at room temperature. The degree of binding was estimated based on comparison of integrated area under the absorption curve for the solutions incubated and non-contacted with heparin.

Results for selected pyridinium compounds and nicotinamide metabolites are presented in a Tables 2 and 3 below.

TABLE 2

The degree of binding of 3-substituted pyridinium salts and selected nicotinamide metabolites with known anti-thrombotic activity to sepharose immobilized heparin

| Compound | | Degree of binding | Thrombolytic response |
|---|---|---|---|
| | 1-methyl-nicotinamide MNA+ | >45% | yes |
| | 1-methyl-N'-(hydroxymethyl) nicotinamide MNAF+ | >35% | yes |
| | 1-methyl-3-acetyl-pyridine MAP+ | >25% | yes |
| | nicotinic acid NC | >40% | no |
| | nicotinamide N-oxide N—OX | >10% | — |

TABLE 2-continued

The degree of binding of 3-substituted pyridinium salts and selected nicotinamide metabolites with known anti-thrombotic activity to sepharose immobilized heparin

| Compound | | Degree of binding | Thrombolytic response |
|---|---|---|---|
| | 1-methyl-2-pyridone-5-carboxamide 2-PYR | >5% | no |
| | nicotinamide NA | ≈0% | no |

TABLE 3

The degree of binding of trigonelline and its thermal decomposition products to sepharose immobilized heparin

| Pyridinium cation | | Degree of binding | Thrombolytic response |
|---|---|---|---|
| | trigonelline Tryg | ≈0% | no |
| | 1-methylpyridine MP+ | >25% | yes |
| | 1,4-dimethylpyridine 14-DMP+ | >20% | yes |
| | 1,2-dimethylpyridine 12-DMP+ | >15% | — |

TABLE 3-continued

The degree of binding of trigonelline and its thermal decomposition products to sepharose immobilized heparin

| Pyridinium cation | | Degree of binding | Thrombolytic response |
|---|---|---|---|
|  | 4-methyltrigonelline 4MeTryg | >5% | — |

The results presented in Table 2 show that quaternary pyridinium salts defined above have a tendency to bind to heparin, what may imply their capability to interact with vascular endothelium surface and account for their therapeutic effect. The therapeutic effect, especially the thrombolytic response of the compounds presented in Table 2 is well documented (see patent WO 2005/067927 A2) and opposed to non-binding properties of other uncharged nicotinamide metabolites, which do not show any significant anti-thrombotic activity.

Results presented in Table 3 indicate that quaternary pyridinium salts show a tendency to bind with heparin, what may imply their capability to interact with vascular endothelium surface and account for their therapeutic effect.

It can be concluded that it is very likely to expect a strong thrombolytic response for all cationic products present in the trigonelline thermolysate. In the case of two compounds, 1-methylpyridine and 1,4-dimethylpyridine, their binding to heparin is accompanied by anti-thrombotic effect in vivo. Although the simple correlation between these effects cannot be expected, the results obtained so far indicate the lack of thrombolytic response for compounds which do not bind to heparin. Essential factor in the non-specific electrostatic interactions of polyanion with the cation is the presence of the positive charge on nitrogen atom of the pyridinium ring. Compounds with sterically large substituents on ring nitrogen, for example, propyl or benzyl groups, bind weaker with heparin in comparison with their N-methyl substituted analogs or do not bind at all. In the case of zwitter-ionic compounds (e.g. trigonelline) the negative charge of the molecule can neutralize the binding effect of positively charge pyridinium ring.

EXAMPLE 3

The Measurement of Thrombolytic Effects of Trigonelline Thermolysate

Figure 1:
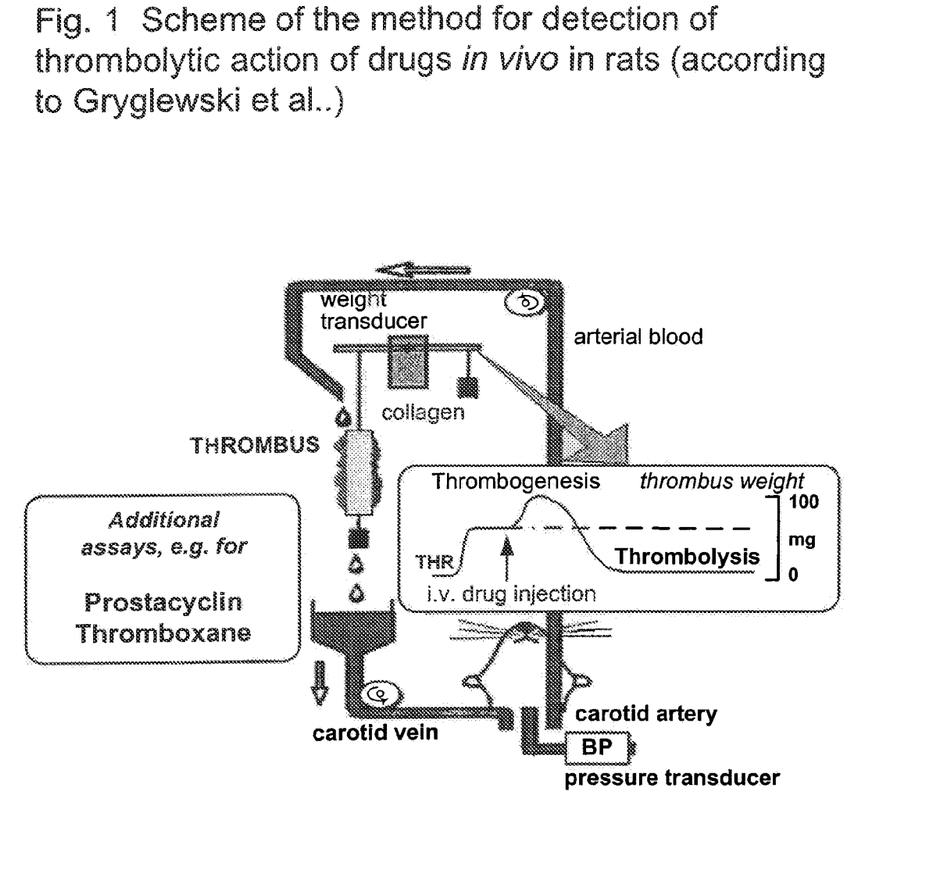
FIG. 1 shows the scheme of the method for detection of thrombolytic action of drugs in vivo in rats.
Figure 2:
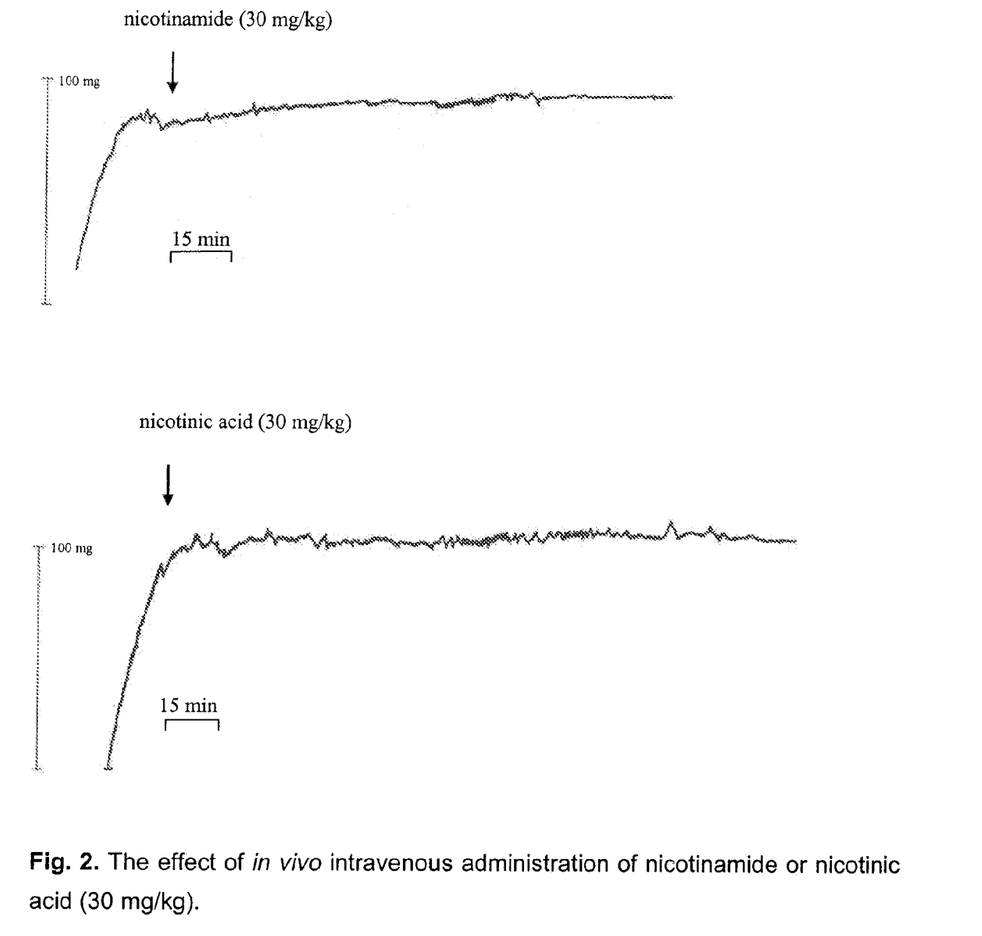
FIG. 2 illustrates the lack of significant thrombolytic response after intravenous administration of nicotinamide or nicotinic acid in vivo (30 mg/kg).
Figure 3:
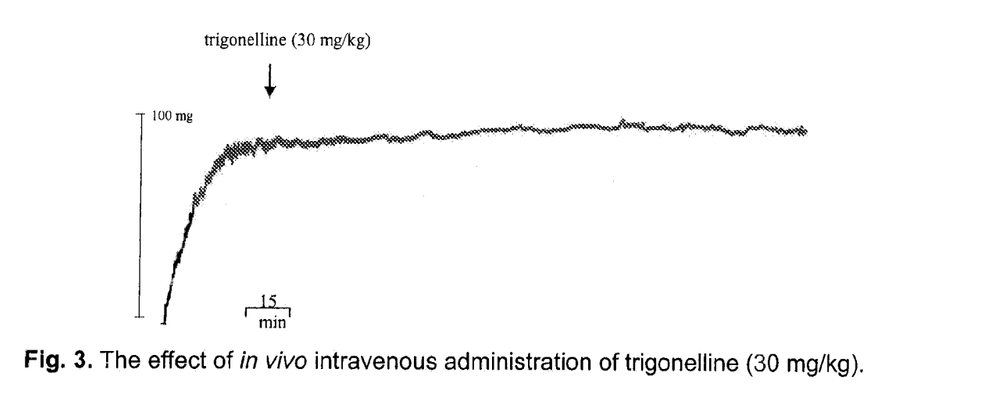
FIG. 3 illustrates the lack of significant thrombolytic response after intravenous administration of trigonelline in vivo (30 mg/kg).
Figure 4:
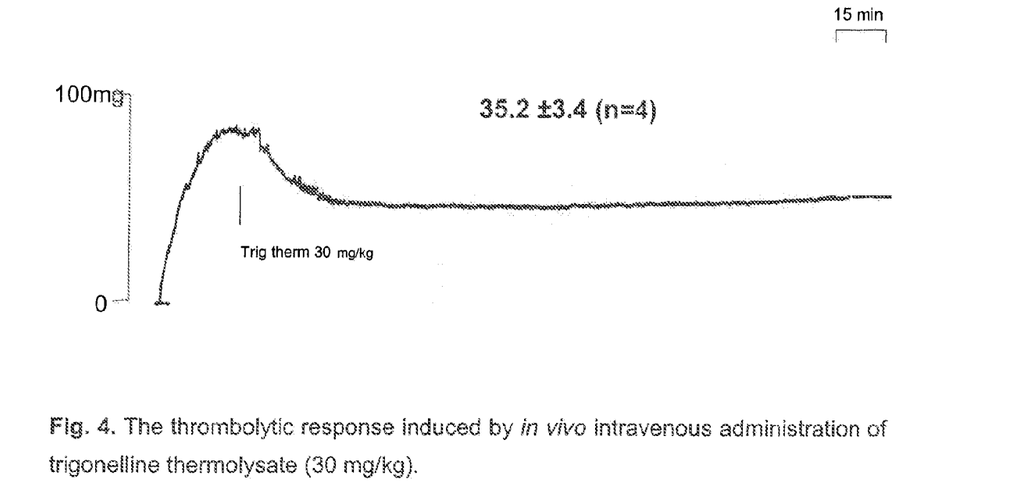
FIG. 4 shows the thrombolytic response induced by intravenous administration of trigonelline thermolysate in vivo (30 mg/kg).
Figure 5:
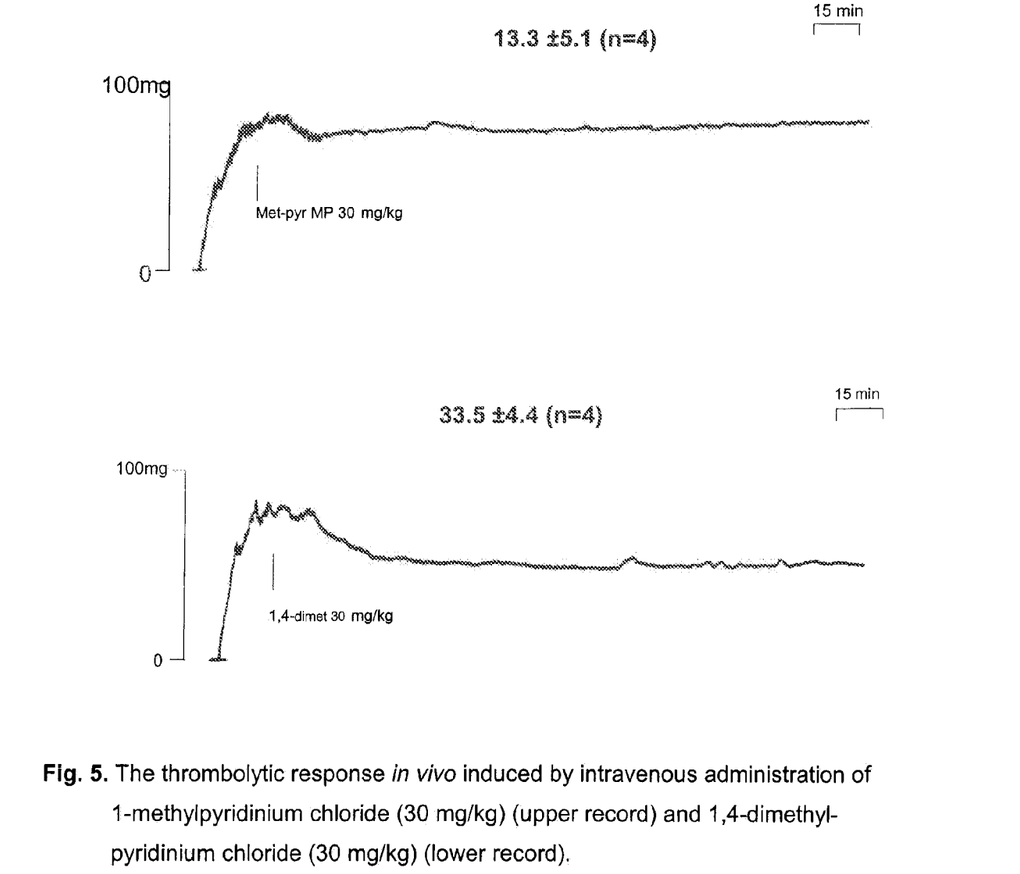
FIG. 5 shows the thrombolytic response in vivo induced by intravenous administration of 1-methylpyridinium chloride (30 mg/kg) (upper record) and 1,4-dimethylpyridinium chloride (30 mg/kg) (lower record).

Thrombolytic activity was assayed by the method developed originally by Gryglewski et al., (Gryglewski R J, Korbut R, Ocetkiewicz A, Stachura J. In vivo method for quantitation for anti-platelet potency of drugs. *Naunyn Schmiedebergs Arch Pharmacol* 1978; 302:25-30; Gryglewski R J 1978, Gryglewski et al., 2001). The scheme of the method is shown on FIG. 1.

Wistar rats (body weight of 300-350 g) were anaesthetised (thiopental 95 mg/kg i.p) and heparinised (800 U/kg i.v.). Caniules were placed in arteries and connected from the left carotid artery vein with a pressure sensor and from the right carotid artery through heated (37° C.) line to peristaltic pomp. The blood from carotid artery was pumped to the extracorporeal circulation were it superfused (1.5 ml/min) a 3 cm collagen strip excised from Achilles tendon hung on a spring-balanced auxotonic lever of a Harvard 386 isotonic transducer and the weight of the collagen strip was continuously registered. After superfusion the blood was returned to the circulation of an animal. During superfusion a thrombus made of platelets aggregates stuck in the fibrin network (microscopically visualized by the Weigert method) was formed on the surface of the collagen strip. A pressure and the thrombus weight were continuously recorded.

After 20-30 min of superfusion the weight of platelet-rich thrombus reached the plateau at the level of approximately 70-100 mg, and this level was steady for 3-5 hours as long as the blood superfusion lasted, unless the active compound was injected intravenously. Then the trigonelline thermolysate, 1-methylpyridine or 1,4-dimethylpyridine were injected intravenously into the femoral vein (30 mg·kg$^{-1}$). Drug-induced thrombolytic effect was observed as a decrease of the weight of the thrombus.

Intravenous injection of trigonelline thermolysate, prepared as described in the example 1, induced an thrombolytic response in Wistar rats with extracorporeal circulation. Following a single injection of trigonelline thermolysate (30 mg/kg) thrombolytic response was seen, reaching the plateau of 35±3.5% after 30 min and lasting at approximately that level for 2-3 hours. 1-methylpyridine (30 mg/kg), being a major component of trigonelline thermolysate, also induced a moderate thrombolytic response. 1,4-dimethylpyridine induced a thrombolytic response that was similar in magnitude and pattern to that induced by trigonelline thermolysate. In contrast to trigonelline thermolysate, 1-methylpyridine and 1,4-dimethylpyridine, trigonelline itself (30 mg/kg) did not induce significant thrombolytic response. Thrombolytic response of nicotinamide or nicotinic acid were of short duration (shorter than 15-20 min) and their maxima were only 9±0.6% and 5±0.9%, respectively. No thrombolytic response was seen for trigonelline. Results of these experiments are shown on FIGS. 2 to 5.

EXAMPLE 4

Antidiabetic Effects of Trigonelline Thermolysate in the Rat Model of Metabolic Syndrome Zucker fatty rats (fa/fa) represent widely used model of genetically determined obesity, metabolic syndrome and dyslipidemia that mimics metabolic syndrome (also called insulin resistance syndrome) leading to the development of manifest type-2 diabetes. The diagnostic symptom of insulin resistance is the elevated postprandial hyperglicemia that could be experimentally induced by glucose injection. In humans elevated postprandial hyperglicemia precedes the development of type 2 diabetes and represent a prognostic factor for cardiovascular complications of diabetes. Elevated postprandial hyperglicemia can be observed also in Zucker fatty rats (fa/fa).

Figure 6:
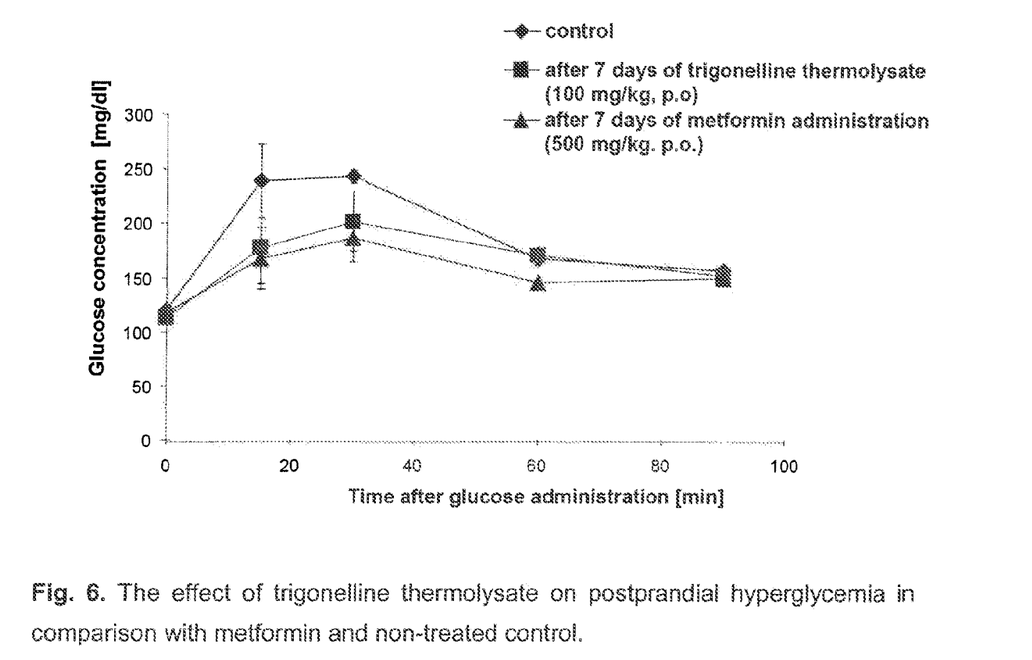
FIG. 6 shows the effect of trigonelline thermolysate on postprandial hyperglycemia in comparison with metformine and non-treated control.

Zucker fatty rats (fa/fa) (Crl:ZUC(Orl)—Lepra) at the age of 10 weeks were treated for 7 days with trigonelline thermolysate (100 mg/kg) (obtained as described in the example 1), with metformin (500 mg/kg) or were left untreated (n=3-4 rats in each experimental group). After 7 days glucose was injected at 2 g/kg (i.p.) and postprandial hyperglycemia was analyzed in the following periods: 0, 15, 30, 60 and 90 minutes after the injection of glucose. As shown in FIG. 6, treatment with trigonelline thermolysate (100 mg/kg) decreased postprandial hyperglycemia induced by glucose injection to the similar degree as it was the case with metformin (500 mg/kg). Accordingly, trigonelline thermolysate possesses antidiabetic properties.

Treatment with trigonelline thermolysate had no effect on the plasma levels of triglycerides or free fatty acid, which were 3.5±0.2, 1.3±0.09 mmol/l and 4.1±0.3, 1.4±0.07 mmol/l for control rats and rats treated with trigonelline thermolysate, respectively.

EXAMPLE 5

Figure 7:
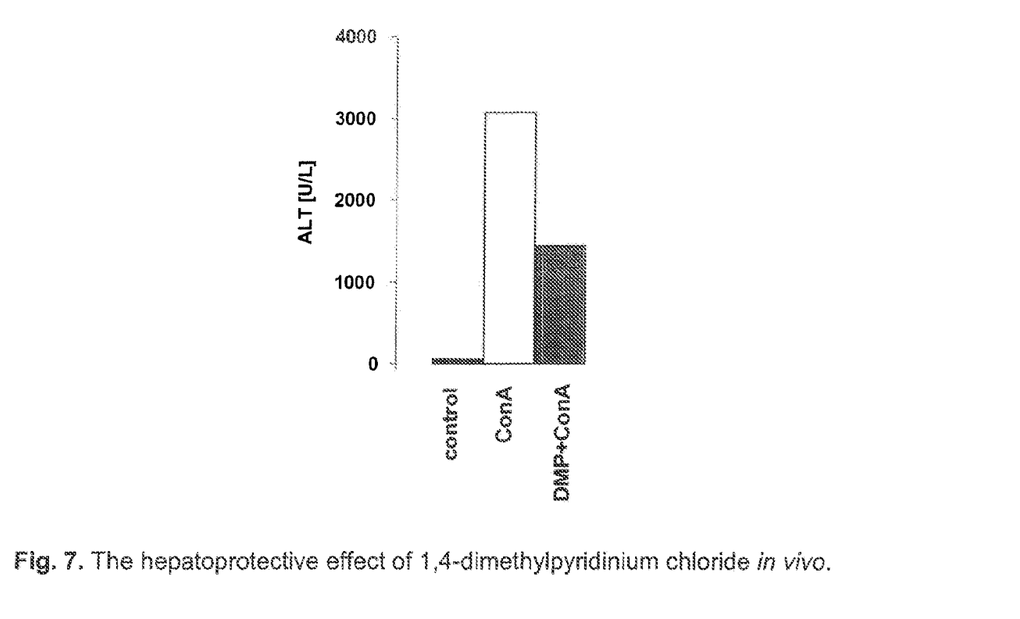
FIG. 7 shows the hepatoprotective effect of 1,4-dimethylpyridinium chloride in vivo.

Hepatoprotective Effects of 1,4-Dimethylpyridinium Chloride in Mice Model of Acute Liver Injury Balb/c mice at the age of 2 months were treated for 7 days with 1,4-dimethylpyridinium chloride (100 mg/kg, per os) or were left untreated and then mice were injected with Concanavalin A (ConA) inducing T cell-mediated hepatitis. ConA was injected intravenously at a dose of 20 mg/kg and 8 hours later liver injury was assessed on the basis of transaminase (AST) level in plasma. As shown in FIG. 7, treatment with 1,4-dimethylpyridinium chloride (100 mg/kg) prevented a rise in AST levels after Con A injection. Accordingly, 1,4-dimethylpyridinium possesses hepatoprotective activity.

What is claimed is:

1. A method of treatment for providing a hepatoprotective effect against liver injury, which method comprises administering to a patient in need thereof an effective amount of a compound selected from the group consisting of:

wherein R represents hydrogen atom, CH₃, OH, pyridyl (C₅H₄N), or pyridyl substituted with hydroxy group ((OH)C₅H₃N), and X represents a physiologically acceptable counterion, wherein said liver injury is acute liver failure, chronic liver failure, liver cirrhosis, drug-induced liver injury, alcohol-induced liver injury, toxic liver injury or liver injury caused by viral hepatitis.

2. The method according to claim 1 wherein said administration is via oral route.

3. The method according to claim 1 wherein said administration is via parenteral route.

4. The method according to claim 1 wherein said compound is the compound of formula (I)

wherein R represents hydrogen atom or CH₃ in the position 2 or 4 of the pyridine ring.

5. The method according to claim 1 wherein R represents CH₃ in the position 4 of the pyridine ring.

6. The method of claim 1 wherein X— represents chloride anion.

7. A method of treatment for providing a hepatoprotective effect against liver injury, which method comprises administering to a patient in need thereof an effective amount of a 1,4-dimethylpyridine salt of the formula (I)

wherein R represents hydrogen atom or CH₃ in the position 2 or 4 of the pyridine ring, wherein said liver injury is acute liver failure, chronic liver failure, liver cirrhosis, drug-induced liver injury, alcohol induced liver injury, toxic liver injury, or liver injury caused by viral hepatitis.

8. The method according to claim 1 wherein R represents CH₃ in the position 4 of the pyridine ring.

9. The method of claim 7 wherein X— represents chloride anion.

10. The method according to claim 7 wherein said administration is via oral route.

11. The method according to claim 7 wherein said administration is via parenteral route.

* * * * *